United States Patent
Hervé et al.

(10) Patent No.: US 9,016,146 B2
(45) Date of Patent: Apr. 28, 2015

(54) METHOD FOR INJECTING A SAMPLE BEING ANALYZED INTO THE INJECTION TUBE OF A MEASUREMENT CELL, IN PARTICULAR OF A DENSIMETER

(75) Inventors: Cleris Hervé, Curcy sur Orne (FR); Marie Patrick, Rots (FR)

(73) Assignee: Instrumentation Scientifique de Laboratoire, Carpiquet (FR)

( * ) Notice: Subject to any disclaimer, the term of this patent is extended or adjusted under 35 U.S.C. 154(b) by 609 days.

(21) Appl. No.: 13/173,175

(22) Filed: Jun. 30, 2011

(65) Prior Publication Data

US 2012/0073389 A1 Mar. 29, 2012

(30) Foreign Application Priority Data

Jul. 2, 2010 (FR) ...................................... 10 55362

(51) Int. Cl.
*G01N 35/10* (2006.01)
*G01N 9/00* (2006.01)
*B01L 3/02* (2006.01)
*B01L 9/00* (2006.01)

(52) U.S. Cl.
CPC ................. *G01N 9/00* (2013.01); *B01L 3/0217* (2013.01); *B01L 9/54* (2013.01); *B01L 2300/042* (2013.01); *B01L 2300/044* (2013.01); *B01L 2300/0841* (2013.01); *G01N 35/10* (2013.01); *G01N 35/1065* (2013.01); *G01N 2203/0266* (2013.01)

(58) Field of Classification Search
USPC ................................ 73/64.56, 864.87, 864.21
See application file for complete search history.

(56) References Cited

U.S. PATENT DOCUMENTS

| 4,673,396 | A | * | 6/1987 | Urbaniak | ....................... 604/211 |
| 4,681,741 | A | * | 7/1987 | Hanaway | ....................... 422/509 |
| 7,918,825 | B2 | * | 4/2011 | O'Connor et al. | ............. 604/151 |
| 2003/0233893 | A1 | * | 12/2003 | Bremer et al. | ............. 73/864.21 |

* cited by examiner

*Primary Examiner* — Paul West
(74) *Attorney, Agent, or Firm* — Faegre Baker Daniels LLP

(57) ABSTRACT

A method for injecting a sample being analyzed into the injection tube of a measurement cell which includes an injection opening and a punch. The sample is introduced into a syringe including a plunger, and the syringe is closed by an expendable cap having a male end closed by a strikable closure. The syringe is secured to the support of an injection station aligned with the injection opening, and a pusher displaces the syringe by vertical translation from an upper position to a lower position with the punch perforating the closure of the cap to inject the sample from the syringe into the injection tube.

4 Claims, 2 Drawing Sheets

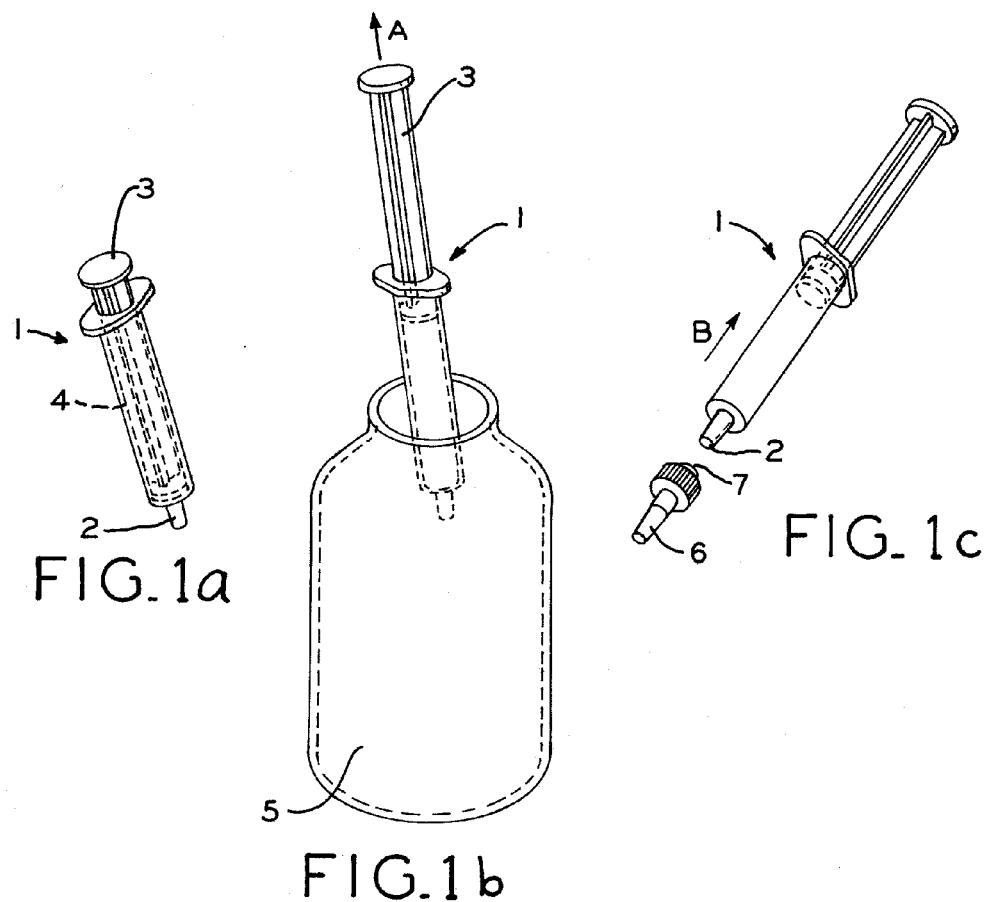
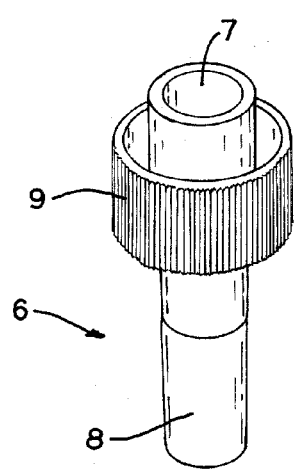
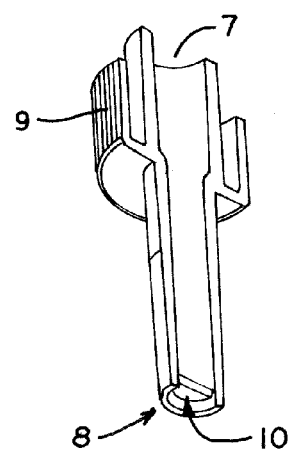

METHOD FOR INJECTING A SAMPLE BEING ANALYZED INTO THE INJECTION TUBE OF A MEASUREMENT CELL, IN PARTICULAR OF A DENSIMETER

CROSS-REFERENCE TO RELATED APPLICATION

This application claims priority to French Patent Application No. 10 55 362 filed Jul. 2, 2010, the disclosure of which is hereby explicitly incorporated by reference herein.

BACKGROUND OF THE INVENTION

1. Field of the Invention

The present invention relates to a method for injecting a sample being analyzed into the injection tube of a measurement cell, in particular of a densimeter.

2. Description of the Related Art

Of the physical measurements which have to be effected in the context of industrial processes, that of density figures among the most frequently necessary.

To that end, manufacturers market a range of densimeters based on various principles, all of which have advantages and disadvantages.

By way of example, a densimeter which can be used in a satisfactory manner to measure the density of a sample is equipped with a measurement cell comprising the following elements:

an isothermic enclosure which defines a measurement chamber at its inner portion;

a U-tube which is to be filled with the sample being analyzed and which extends inside the measurement chamber;

means for causing the U-tube to vibrate; and means for reading the vibratory response of that tube.

The U-tube of a densimeter cell of that type is secured to the measurement chamber at its free ends which project outwardly from that chamber in order to permit the injection of the sample being analyzed via an injection opening and its evacuation via an evacuation opening.

The principle of measuring the density of a sample by means of such a densimeter consists in causing the U-tube to vibrate at resonance frequency and in determining that frequency using the reading means.

The resonance frequency enables the density of the sample being analyzed to be calculated to a first approximation on the basis of a standard equation known per se and from a preliminary calibration of the densimeter.

The injection of a sample being analyzed into the U-tube of a densimeter cell of that type can be effected manually under pressure by means of a simple syringe equipped with an end-piece which is introduced into the injection opening.

However, such an operation is long and inconvenient and may also cause losses of sample.

In order to facilitate this injection, densimeters equipped with a device for the automatic injection under pressure of the samples being analyzed have already been proposed.

Those devices comprise a rotary dispensing carousel equipped at its periphery with a set of containers, in particular cylinders, for receiving samples being analyzed, which containers can be closed by a stopper.

The containers can be positioned successively in alignment with an injection station where they are coupled, on the one hand, to an injection duct connected to the injection opening of the densimeter cell and, on the other hand, to a duct connected to a pressure source.

The introduction of a sample being analyzed into a container provided on the dispensing carousel and the mounting on that container of the injection duct and the pressurising duct at the injection station are, however, long and tricky operations.

In parallel with those pressurised-injection devices, it has also already been proposed to inject the samples being analyzed into the densimeter cell under vacuum by connecting the evacuation opening of the U-tube to a vacuum source, in particular to a vacuum pump.

In such vacuum-injection devices, a container holding the sample being analyzed can be coupled to the injection opening of the U-tube via an injection duct.

Such devices have, however, the disadvantage of being suitable for analysing only low-viscosity samples and of requiring after each measurement a long and inconvenient rinsing step which additionally involves the use of a large amount of solvent, which is detrimental to the environment.

Also currently on the market are densimeters equipped with vacuum-injection devices which comprise an automatic dispensing carousel provided at its periphery with a set of containers for receiving samples being analyzed.

Such containers are positioned successively in alignment with an injection station where they are coupled to an injection duct connected to the injection opening of the densimeter cell.

Such devices having an automatic dispensing carousel nevertheless have the above-mentioned disadvantages of vacuum-injection devices as regards the impossibility of analysing viscous samples and the requirement to implement rinsing steps which necessitate large quantities of solvents.

In addition, the introduction of a sample being analyzed into a container provided on the dispensing carousel, and the mounting of the injection duct on that container at the injection station are again long and tricky operations.

SUMMARY OF THE INVENTION

The present invention provides a method for injecting a sample being analyzed into the injection tube of a densimeter.

It should be noted that this method is not limited to the injection of samples being analyzed into a densimeter cell equipped with a U-tube of the above-mentioned type but can be adapted more generally to any measurement cell equipped with an injection tube which extends substantially vertically upwards and which is provided, at its free end projecting to the outside, with an opening for injecting a sample being analyzed.

According to this method, a standard single-use syringe is used to inject the sample being analyzed into the injection opening of the tube of the measurement cell and comprises a pump body which is extended by a male end-piece and in which a plunger is displaced.

The method is based on two fundamental steps including equipping the injection tube of the measurement cell with a punch at its inner portion, at the injection opening, this being done at the construction stage, and closing the syringe, after the sample being analyzed has been introduced into it, by means of an expendable luer-type cap comprising a female end receiving the end-piece of the pump body, as well as a male end closed by a strikable closure.

Such a standard syringe and such an expendable cap are particularly inexpensive elements.

According to the invention, the syringe thus closed by an expendable cap and containing the sample being analyzed is secured substantially vertically, with the cap lowermost, to a support provided on an injection device.

The injection device comprises an injection station located in alignment with the injection opening of the injection tube and provided with a pusher.

At that station, the syringe positioned on the support can be displaced by vertical translation from an upper position or positioning position to a lower position or injection position.

The following step of the method according to the invention consists in positioning the support thus equipped with the syringe in the upper position in alignment with the injection station so that the plunger of the syringe is facing the pusher and the cap is facing the injection opening of the injection tube.

The syringe is then displaced into the lower position so that the punch perforates the closure of the cap, then the pusher is operated in order to displace the plunger of the syringe downwardly and to inject the sample contained therein into the injection tube of the measurement cell.

The implementation of the method according to the invention is particularly easy both as regards the filling of the syringe from a container holding the sample being analyzed and as regards the introduction of that sample into the injection opening of the injection tube of the measurement cell.

The method also has the advantage of permitting the analysis of viscous as well as weakly viscous samples and of not requiring complex rinsing steps involving the use of large amounts of solvent after each measurement.

According to a further feature of the invention, the female end of the expendable cap is surrounded by a knurled collar the main function of which is to enable the assembly formed by the syringe and the cap to be guided when it is put in place on the support of the injection device.

The knurling at the same time makes it easier to grip the expendable cap and to secure it to the male end-piece of the syringe by pressing.

According to the invention, the injection device equipped with the support may be a device comprising only one feed station or an automatic device comprising several feed stations.

According to a first variant of the invention in which the injection device comprises only one feed station, the support may be a carriage mounted in alignment with the injection station and comprising a housing for receiving a syringe, or also a stationary receptacle equipped with a pivoting slide enabling a syringe to be loaded.

In the first case, the carriage is movable in translation between the upper position and the lower position.

In the second case, the injection station is also equipped with a fork enabling the syringe to be displaced into the lower position.

According to a second variant of the invention in which the injection device comprises several feed stations, the support is a rotary dispensing carousel comprising at its periphery a set of housings for receiving a syringe, which housings can be positioned successively in alignment with the injection station.

In one form thereof, the present invention provides a method for injecting a sample being analyzed into the injection tube of a measurement cell, in particular of a densimeter, the injection tube extending vertically upwards and being equipped at its free end projecting to the outside with an opening for injecting a sample being analyzed, characterized by the following steps:

the injection tube is equipped with a punch at its inner portion, at the injection opening (15);
the sample being analyzed is introduced into a standard single-use syringe (1), the syringe (1) comprising a pump body (4) which is extended by a male end-piece (2) and in which a plunger (3) is displaced;
the syringe (1) is closed by means of an expendable luer-type cap (6) comprising, on the one hand, a female end (7) receiving the end-piece (2) of the pump body (4) and, on the other hand, a male end (8) closed by a strikable closure (10);
the syringe (1) thus closed is secured substantially vertically, with the cap (6) lowermost, to a support provided on an injection device, the injection device comprising an injection station (12) which is located in alignment with the injection opening (15) of the injection tube and which is provided with a pusher (16), and at which the syringe (1) positioned on the support can be displaced by vertical translation from an upper position or positioning position to a lower position or injection position;
the support is positioned in alignment with the injection station (12) so that the plunger (3) of the syringe (1) is facing the pusher (16) and the cap (6) is facing the injection opening (15) of the injection tube;
the syringe (1) is displaced into the lower position so that the punch perforates the closure (10) of the cap (6); and
the pusher (16) is operated in order to displace the plunger (3) of the syringe (1) downwardly and to inject the sample contained therein into the injection tube.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIGS. 1a, 1b and 1c are diagrams illustrating the first steps of the implementation of the method according to the invention;

FIG. 2 is a perspective view of an expendable cap;

FIG. 3 is a sectioned view of that same cap;

Figure 4:
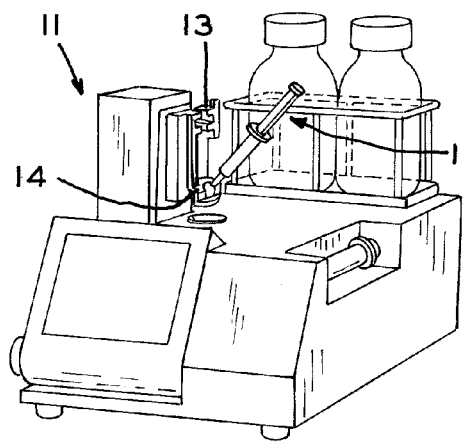
FIG. 4 shows an apparatus for measuring the density of a sample which comprises only one feed station.

Corresponding reference characters indicate corresponding parts throughout the several views. Although the exemplifications set out herein illustrate embodiments of the invention, in several forms, the embodiments disclosed below are not intended to be exhaustive or to be construed as limiting the scope of the invention to the precise forms disclosed.

DETAILED DESCRIPTION

According to FIG. 1a, in order to implement the method according to the invention, a single-use standard syringe 1 comprising a pump body 4 which is extended by a male end-piece 2 and in which a plunger 3 is displaced is used.

According to FIG. 1b, the first step of this method consists in taking the sample being analyzed from a container 5 using the syringe 1 by displacing the plunger 3 as shown diagrammatically by the arrow A.

According to FIG. 1c, the second step of this method consists in closing the male end-piece 2 of the syringe 1 by means of an expendable luer-type cap 6 as shown diagrammatically by the arrow B.

According to FIG. 2, the expendable cap 6 comprises a female end 7, which receives the end-piece 2 of the syringe 1, and also a male end 8.

The female end 7 of the expendable cap 6 is surrounded by a knurled collar 9.

According to FIG. 3, the male end 8 of the expendable cap 6 is closed by a strikable closure 10.

Figure 5:
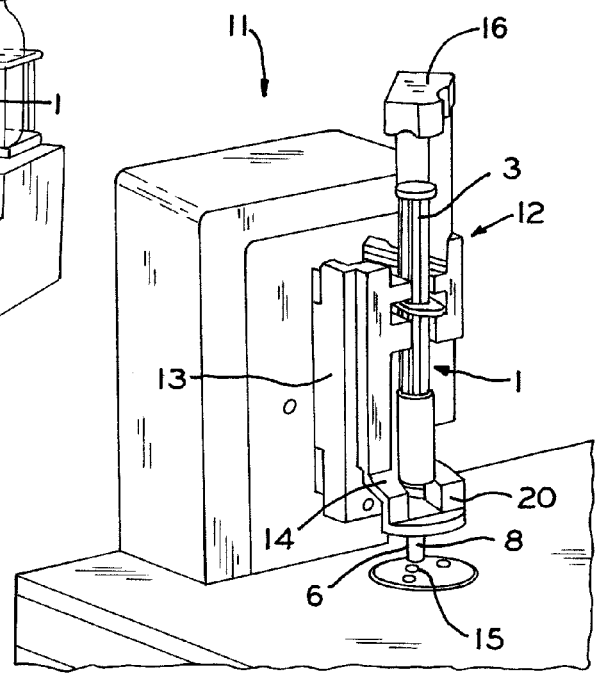
FIG. 5 shows the injection station of the apparatus represented in FIG. 4.

As shown in FIGS. 4 and 5 according to the first variant of the invention, the injection method is implemented in an apparatus for measuring the density of a sample being analyzed 11 which comprises only one feed station.

According to FIG. 5, the measurement apparatus 11 comprises a measurement cell into which the sample being analyzed is introduced via an injection opening 15, and also an injection station 12.

In a manner not shown in the Figures, the injection opening 15 is equipped with a punch at its inner portion.

The injection station 12 is equipped with a carriage 13 which is movable in vertical translation between an upper position and a lower position and which is arranged in alignment with the injection opening 15, and also with a pusher 16.

The carriage 13 comprises a housing 14 for receiving a syringe 1 which is equipped with an expendable cap 6 and which is positioned vertically, with the plunger 3 uppermost, and also an opening 20 for holding the collar 9 of the cap.

To that extent, the carriage 13 forms the feed station of the apparatus.

As shown in FIG. 5, when a syringe 1 is positioned in the receiving housing 14, the pusher 16 is facing the end of the plunger 3.

According to FIG. 4, when the method according to the invention is implemented, the technician presents a syringe 1, previously filled with a sample and closed by an expendable cap 6, in alignment with the receiving housing 14, then, according to FIG. 5, he positions it vertically in the holding opening 20 so that it is secured in the carriage 13 which is then in the upper position.

During that step, the knurled collar 9 which surrounds the female end 7 of the expendable cap 6 guides the positioning of the syringe in the carriage 13.

In the following step, the carriage 13 automatically displaces the syringe 1 into the lower position so that the male end 8 of the expendable cap 6 penetrates into the injection opening 15.

In the course of that displacement, the punch mounted at the inner portion of the injection opening 15 perforates the closure 10 of the expendable cap 6.

The last step of the method according to the invention consists in operating the pusher 16 in order to displace the plunger 3 of the syringe 1 downwardly and to inject the sample contained therein into the injection tube of the apparatus.

Figure 6:
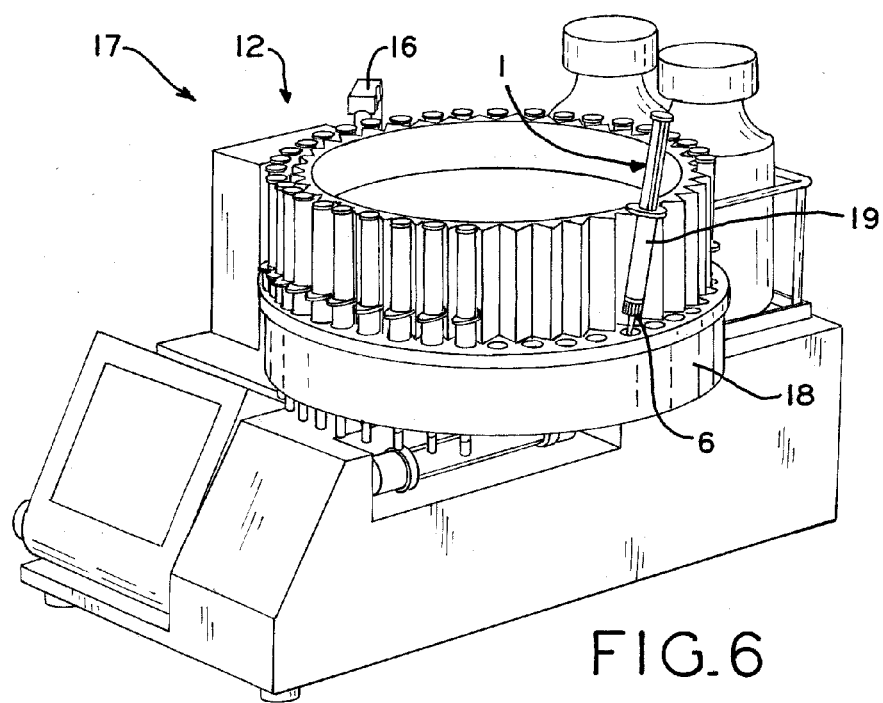
FIG. 6 shows an apparatus for measuring the density of a sample which comprises several feed stations.

According to FIG. 6, the apparatus for measuring the density of a sample 17 being analyzed is an apparatus according to the second variant of the invention; that apparatus is equipped with a rotary dispensing carousel 18 comprising at its periphery a set of housings 19 for receiving a syringe 1 previously filled with a sample being analyzed and equipped with an expendable cap 6.

The rotation of the dispensing carousel 18 enables the receiving housings 19 and the syringes 1 to be brought successively into alignment with an injection station 12 which is basically similar to the one shown in FIG. 5 and which is located in alignment with the injection opening 15.

At that station, a fork (not shown in the Figure) enables the syringe 1 to be lowered so that the male end 8 of the expendable cap 6 penetrates into the injection opening 15 and the closure 10 is perforated by the punch provided in that opening so as to enable the sample being analyzed to be injected into the apparatus.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method for injecting a sample into the injection tube of a measurement cell, the injection tube including an injection opening and a punch, said method comprising the steps of:

introducing the sample into a syringe including a pump body having a. male end piece and a displaceable plunger;

closing the syringe by a cap, the cap including a female end for receiving the end piece of the pump body and a male end closed by a strikable closure;

after said closing step, securing the syringe substantially vertically, with the cap oriented downwardly, to a support provided on an injection device of the measurement cell, the injection device including an injection station aligned with the injection opening of the injection tube and further including a pusher for displacing the plunger of the syringe from an upper, positioning position to a lower, injection position;

positioning the support in alignment with the injection station with the plunger facing the pusher and the cap facing the injection opening of the injection tube;

after said positioning step, displacing the syringe to a lower syringe position, wherein the punch perforates the closure of the cap; and operating the pusher to displace the plunger of the syringe downwardly to inject the sample into the injection tube.

2. The method of claim 1, wherein the female end of the cap is surrounded by a knurled collar.

3. The method of claim 1, wherein the support is a carriage movable in vertical translation between the upper position and the lower position, the carriage mounted in alignment with the injection station and including a housing for receiving a syringe.

4. method according to claim 1, wherein the step of closing the syringe by a cap further comprises sealingly closing the male end piece of the syringe by a removable cap removably coupled to the syringe.

* * * * *